US009572481B2

(12) United States Patent
Duindam et al.

(10) Patent No.: US 9,572,481 B2
(45) Date of Patent: Feb. 21, 2017

(54) MEDICAL SYSTEM WITH MULTIPLE OPERATING MODES FOR STEERING A MEDICAL INSTRUMENT THROUGH LINKED BODY PASSAGES

(75) Inventors: Vincent Duindam, Oakland, CA (US); Giuseppe Maria Prisco, Mountain View, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 261 days.

(21) Appl. No.: 13/107,052

(22) Filed: May 13, 2011

(65) Prior Publication Data
US 2012/0289783 A1    Nov. 15, 2012

(51) Int. Cl.
| | | |
|---|---|---|
| A61B 1/00 | (2006.01) |
| A61B 1/04 | (2006.01) |
| A61M 31/00 | (2006.01) |
| A61B 1/01 | (2006.01) |
| A61B 1/005 | (2006.01) |
| A61B 5/06 | (2006.01) |

(52) U.S. Cl.
CPC ......... *A61B 1/00147* (2013.01); *A61B 1/0051* (2013.01); *A61B 1/01* (2013.01); *A61B 5/065* (2013.01)

(58) Field of Classification Search
CPC ..... A61B 1/01; A61B 1/0051; A61B 19/2203; A61B 19/5244; A61B 2017/00026; A61B 2019/2211; A61B 2019/2242; A61B 2019/2276; A61B 2019/464; A61B 2019/505; A61B 2019/507; A61B 2019/5251; A61B 5/6885

USPC ....... 600/146, 114, 117, 145, 118, 152, 585; 604/510; 227/2, 107
See application file for complete search history.

(56) References Cited

U.S. PATENT DOCUMENTS

| | | |
|---|---|---|
| 5,078,140 A | 1/1992 | Kwoh |
| 5,188,111 A | 2/1993 | Yates et al. |
| 5,347,987 A | 9/1994 | Feldstein et al. |

(Continued)

FOREIGN PATENT DOCUMENTS

| | | |
|---|---|---|
| CN | 101198370 A | 6/2008 |
| CN | 101227854 A | 7/2008 |

(Continued)

OTHER PUBLICATIONS

Bettini, Alessandro et al., "Vision Assisted Control for Manipulation Using Virtual Fixtures," IEEE Transactions on Robotics, 2004, pp. 953-966, vol. 20—Issue 6, IEEE.

(Continued)

*Primary Examiner* — John P Leubecker
*Assistant Examiner* — Arnaldo Torres Diaz

(57) ABSTRACT

A controller operates in different operating modes to control movement of a distal tip of a medical instrument when inserting and retracting the medical instrument through linked body passages. When inserting the medical instrument, the controller normally operates in an automatic navigation mode unless manually overridden to operate in a manual mode. When retracting the medical instrument, the controller normally operates in a zero-force mode to allow the distal tip to freely move so that it may comply with the shape of the passages as the medical instrument is being retracted through the linked body unless manually overridden to operate in a manual mode.

19 Claims, 5 Drawing Sheets

(56) References Cited

U.S. PATENT DOCUMENTS

| | | |
|---|---|---|
| 5,350,355 A | 9/1994 | Sklar |
| 5,396,879 A | 3/1995 | Wilk et al. |
| 5,431,645 A * | 7/1995 | Smith et al. ............... 606/1 |
| 6,120,433 A | 9/2000 | Mizuno et al. |
| 6,152,920 A | 11/2000 | Thompson et al. |
| 6,231,563 B1 * | 5/2001 | White et al. ............... 604/523 |
| 6,468,203 B2 * | 10/2002 | Belson ........................ 600/146 |
| 6,610,007 B2 * | 8/2003 | Belson et al. ............... 600/146 |
| 6,800,056 B2 | 10/2004 | Tartaglia et al. |
| 6,810,281 B2 | 10/2004 | Brock et al. |
| 6,843,793 B2 * | 1/2005 | Brock et al. ............... 606/130 |
| 6,869,396 B2 * | 3/2005 | Belson ........................ 600/146 |
| 6,920,347 B2 | 7/2005 | Simon et al. |
| 6,929,634 B2 * | 8/2005 | Dorros et al. ............... 604/523 |
| 6,974,411 B2 * | 12/2005 | Belson ........................ 600/114 |
| 6,984,203 B2 | 1/2006 | Tartaglia et al. |
| 7,044,907 B2 | 5/2006 | Belson |
| 7,063,714 B2 * | 6/2006 | Dorros et al. ............... 606/194 |
| 7,087,013 B2 * | 8/2006 | Belson et al. ............... 600/145 |
| 7,101,361 B2 * | 9/2006 | Gardeski .................... 604/523 |
| 7,320,688 B2 * | 1/2008 | Foley et al. ............... 606/99 |
| 7,338,505 B2 | 3/2008 | Belson |
| 7,789,875 B2 * | 9/2010 | Brock et al. ............... 606/1 |
| 7,887,549 B2 * | 2/2011 | Wenderow et al. ......... 606/108 |
| 7,901,348 B2 | 3/2011 | Soper et al. |
| 2002/0087048 A1 * | 7/2002 | Brock et al. ............... 600/114 |
| 2002/0143319 A1 | 10/2002 | Brock |
| 2003/0013949 A1 | 1/2003 | Moll et al. |
| 2003/0069475 A1 | 4/2003 | Banik et al. |
| 2005/0182319 A1 * | 8/2005 | Glossop ..................... 600/424 |
| 2005/0222498 A1 * | 10/2005 | Belson ........................ 600/117 |
| 2006/0089531 A1 * | 4/2006 | Tartaglia et al. ............ 600/114 |
| 2007/0156019 A1 * | 7/2007 | Larkin et al. ............... 600/104 |
| 2007/0198008 A1 * | 8/2007 | Hauck et al. ............... 606/41 |
| 2007/0213584 A1 * | 9/2007 | Kim et al. .................... 600/104 |
| 2007/0287992 A1 * | 12/2007 | Diolaiti et al. ............... 606/1 |
| 2008/0004595 A1 * | 1/2008 | Viswanathan et al. ....... 604/500 |
| 2008/0097159 A1 * | 4/2008 | Ishiguro ....................... 600/145 |
| 2008/0212082 A1 * | 9/2008 | Froggatt et al. ............. 356/73.1 |
| 2008/0218770 A1 * | 9/2008 | Moll et al. .................... 356/614 |
| 2008/0221592 A1 * | 9/2008 | Kawai ......................... 606/130 |
| 2009/0324161 A1 * | 12/2009 | Prisco ......................... 385/13 |
| 2010/0069719 A1 | 3/2010 | Wehrheim |
| 2010/0121148 A1 | 5/2010 | Donhowe et al. |
| 2010/0222668 A1 * | 9/2010 | Dalke et al. ................. 600/424 |
| 2010/0249506 A1 | 9/2010 | Prisco |
| 2010/0249507 A1 | 9/2010 | Prisco et al. |
| 2010/0274087 A1 * | 10/2010 | Diolaiti et al. ............... 600/118 |
| 2011/0040305 A1 * | 2/2011 | Gomez et al. ............... 606/130 |
| 2011/0040404 A1 * | 2/2011 | Diolaiti et al. ............... 700/245 |
| 2012/0022329 A1 * | 1/2012 | Wagh et al. ................. 600/118 |
| 2013/0012925 A1 * | 1/2013 | Berthiaume et al. ......... 604/529 |

FOREIGN PATENT DOCUMENTS

| | | |
|---|---|---|
| EP | 2165641 A2 | 3/2010 |
| JP | H03109023 A | 5/1991 |
| JP | 2002236260 A | 8/2002 |
| JP | 2004180940 A | 7/2004 |
| JP | 2008541797 A | 11/2008 |
| WO | WO9501757 | 1/1995 |
| WO | WO-03028547 A2 | 4/2003 |
| WO | 04000107 A2 | 12/2003 |
| WO | WO2008098085 A2 | 8/2008 |
| WO | WO2008133956 A2 | 11/2008 |
| WO | WO2009037576 A2 | 3/2009 |
| WO | WO2009097461 A1 | 8/2009 |

OTHER PUBLICATIONS

Burschka, Darius et al., "Navigating Inner Space: 3-D Assistance for Minimally Invasive Surgery," Robotics and Autonomous Systems, 2005, pp. 5-26, vol. 52—Issue 1, Elsevier.

Dodds, Zachary et al., "A hierarchical architecture for vision-based robotic manipulation tasks," in Proceedings of the International Conference on Vision Systems, 1999, pp. 312-330, vol. 542, Springer-Verlag.

Funda, Janez et al., "Optimal Motion Control for Teleoperated Surgical Robots," Intl. Symp. on Optical Tools for Manuf. & Adv Autom,Telemanipulator Technology and Space Telerobotics, 1993, pp. 211-222, vol. 2057, SPIE.

Marayong, Panadda et al., "Spatial Motion Constraints: Theory and Demonstrations for Robot Guidance Using Virtual Fixtures," IEEE International Conference on Robotics and Automation Robotics and Automation, 2003, pp. 1954-1959, vol. 2, No. 14-19, IEEE.

Taylor, Russell H. et al., "Medical Robotics and Computer-Integrated Surgery," Chapter 52 in Springer Handbook of Robotics, Springer, 2008, pp. 1199-1222.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

International Search Report and Written Opinion for Application No. PCT/US2012/035400, mailed on Nov. 14, 2012, 11 pages.

Extended European Search Report for Application No. EP12786742, mailed on Oct. 6, 2014, 6 pages.

\* cited by examiner

MEDICAL SYSTEM WITH MULTIPLE OPERATING MODES FOR STEERING A MEDICAL INSTRUMENT THROUGH LINKED BODY PASSAGES

FIELD OF THE INVENTION

The present invention generally relates to medical systems and in particular, to a medical system with multiple operating modes for steering a medical instrument through linked body passages.

BACKGROUND

One type of medical instrument that is steered through body passages is an endoscope. Endoscopes allow physicians to capture images of and diagnose problems with internal body organs by inserting the device either through a natural orifice or a surgeon created opening and guiding it to a target site within a patient. In some cases, it may also be used to perform medical procedures on the internal body organs. It may be steerable so that its distal tip is controllably oriented for navigation purposes. An image capturing device such as a stereoscopic or monoscopic camera may be provided at its distal tip so that images captured by the camera from that perspective may be viewed on a display screen by the surgeon. To perform various medical procedures at the target site, surgical tools, such as those used for cutting, grasping, cauterizing, etc., may extend out of the endoscope's distal tip.

Specialized endoscopes may be named for where they are generally intended to look. Examples include: cystoscopes for looking in the bladder, nephroscopes for looking in the kidney, bronchoscopes for looking in bronchi of the lung, laryngoscopes for looking in the larynx, otoscopes for looking in the ear, arthroscopes for looking at joints, laparoscopes for looking inside the abdomen, and gastrointestinal endoscopes. In order to look at their intended organs, endoscopes may move through linked body passages in the body to a target area.

Another type of medical instrument that is steerable through body passages is a catheter. Catheters are long slender flexible tubes that are inserted into a natural bodily cavity or passage for introducing or withdrawing fluid. Its uses include the drainage of urine from the bladder through the urethra or insertion through a blood vessel into the heart for diagnostic purposes. Catheters may also be inserted in a passage to keep the passage open.

Still other types of medical instruments that are steerable through body passages are surgical and diagnostic tools. Examples include such common medical implements as forceps for taking tissue samples and electrodes used for cauterization of tissue.

Body passages through which such medical instruments are steered may be circuitous and have varying widths along their lengths. Further, they may be multi-branched and narrow so that navigation to target areas in the body is difficult. Also, the passage may comprise sensitive tissue that is easily harmed by excessive physical contact with the medical instrument. As an example of linked body passages, U.S. Pat. No. 7,901,348 B2 describes visual-assisted guidance of an ultra-thin flexible endoscope to a predetermined region of interest within the bronchial tree of a lung during a bronchoscopy procedure. As other examples of linked body passages, U.S. 2005/0182319 A1 describes image guided surgery techniques applicable to the blood circulatory system as well as the air circulatory system of the lung, the digestive system, and the urinary system.

When an operator is inserting a medical instrument through linked body passages to a target area in an anatomical structure of a patient, it may be desirable to assist the operator in navigating the medical instrument to the target area. In retracting the medical instrument back out of the linked body passages, care must be taken to avoid harming the passage walls by excessive physical contact with the medical instrument. Safety for the patient is a primary concern at all times while controlling movement of the medical instrument in the patient.

OBJECTS AND SUMMARY

Accordingly, one object of one or more aspects of the present invention is a medical system, and method implemented therein, for controlling the movement of a medical instrument through body passages without causing harm to a patient.

Another object of one or more aspects of the present invention is a medical system, and method implemented therein, for providing navigation assistance when useful to an operator for steering a medical instrument to and/or from a target area through linked body passages in a safe and efficient manner.

Still another object of one or more aspects of the present invention is a medical system, and method implemented therein, for providing automatic navigation assistance with manual override to a target area through linked body passages.

These and additional objects are accomplished by the various aspects of the present invention, wherein briefly stated, one aspect is a medical system comprising: a steerable medical instrument; at least one actuator; and control means for commanding the at least one actuator to cause the medical instrument to be steered according to an insertion control mode after movement of the medical instrument is detected in an insertion direction and commanding the at least one actuator to allow the medical instrument to move in compliance with forces exerted against the medical instrument after movement of the medical instrument is detected in a retraction direction.

Another aspect is a method for controlling the steering of a medical instrument, the method comprising: detecting movement of the medical instrument; and commanding at least one actuator to cause the medical instrument to be steered according to an insertion control mode after movement of the medical instrument is detected in an insertion direction and commanding the at least one actuator to allow the medical instrument to move in compliance with forces exerted against the medical instrument after movement of the medical instrument is detected in a retraction direction.

Another aspect is a medical system comprising: an input device; a medical instrument; at least one actuator; and control means for commanding the at least one actuator to cause the medical instrument to be steered according to a programmed navigation path in a normal control mode and for commanding the at least one actuator to cause the medical instrument to be steered according to movement of the input device commanding such steering when the normal control mode is manually overridden by an operator of the input device.

Yet another aspect is a method for controlling the steering of a medical instrument, the method comprising: commanding at least one actuator to steer the medical instrument according to a programmed navigation path while being moved in an insertion direction; receiving a manual override indication; and commanding the at least one actuator to steer the medical instrument according to movement of an input device.

Additional objects, features and advantages of the various aspects of the present invention will become apparent from the following description of its embodiments which description should be taken in conjunction with the accompanying drawings.

BRIEF DESCRIPTION OF THE DRAWINGS

FIG. 3 illustrates a diagram of linked body passages through which a medical instrument may pass through.

DETAILED DESCRIPTION

Figure 1:
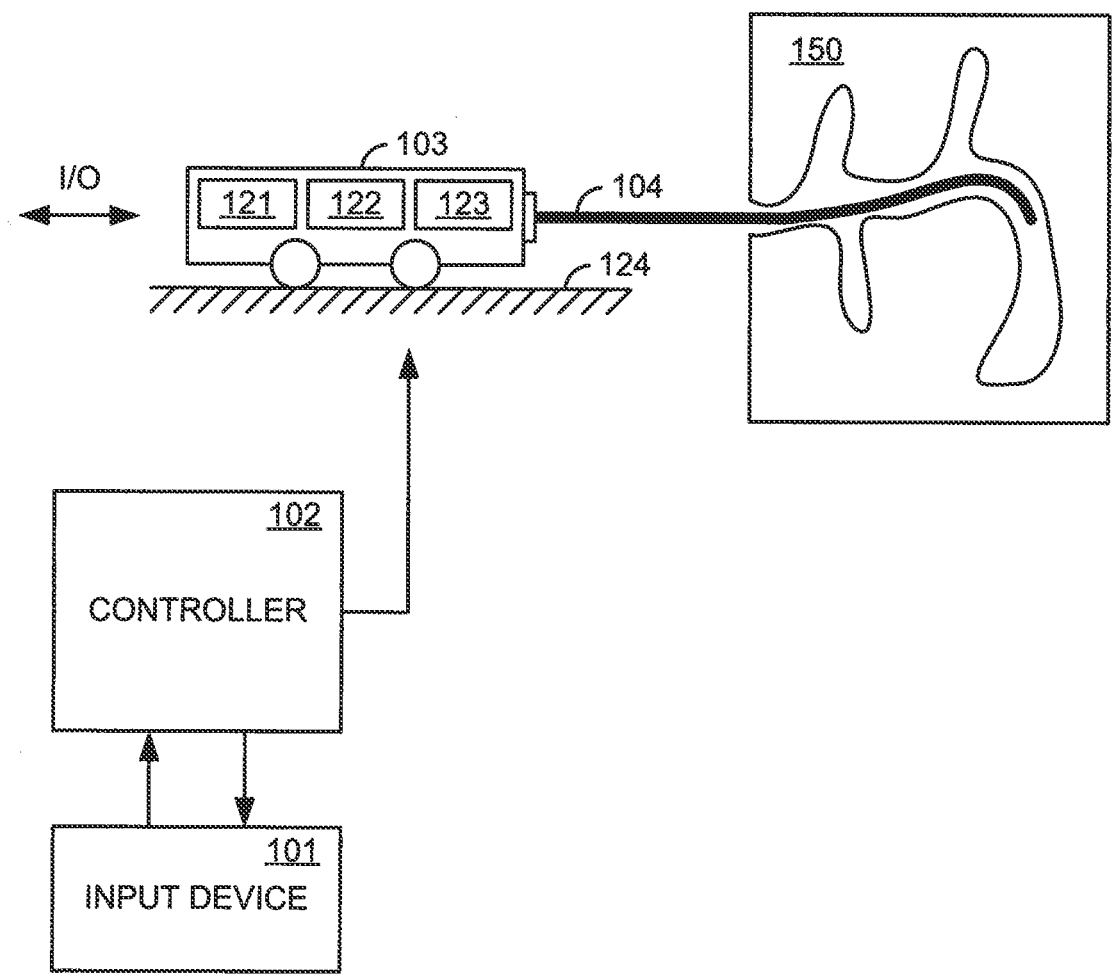
FIG. 1 illustrates a diagram of a medical instrument which is disposed within linked body passages and controlled by a controller of a medical system utilizing aspects of the present invention.
Figure 2:
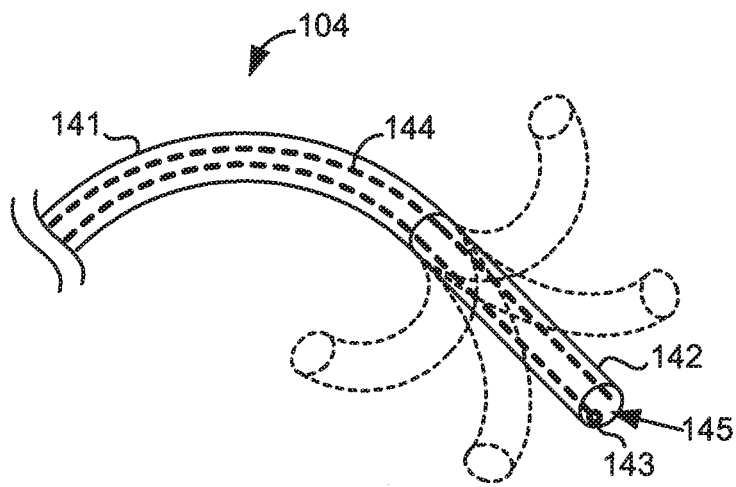
FIG. 2 illustrates a diagram of a distal end of a medical instrument used in a medical system utilizing aspects of the present invention.

FIG. 1 illustrates use of a medical system in which a controller 102 commands actuators 103 to move a medical instrument 104 into and out of and through linked body passages of a patient 150 in response to operator interaction with an input device 101. The medical instrument 104 in this case may be an endoscope, catheter or other medical device having a steerable tip 142 such as shown in FIG. 2. The actuators 103 include an actuator 121 for moving the entire medical instrument 104 along a rail 124 in an input direction (i.e., insertion into the patient 150) and an output direction (i.e., retraction out of the patient 150), as depicted by the two-headed arrow denoted "I/O". Alternatively, the actuator 121 may be omitted, in which case, an operator may manually insert and retract the medical instrument 104 into and out of the linked body passages. The actuators 103 also include actuators 122 and 123 for steering the steerable tip 142.

FIG. 2 illustrates details of a distal end of the medical instrument 104 in which the steerable tip 142 is shown in a non-rotated state in solid line form and in various rotated states in dotted line forms. The medical instrument 104 includes a flexible body 141 to which the steerable tip 142 is rotationally coupled. For example, when the steerable tip 142 is rotated in a pitch direction, it moves as shown in the illustrated dotted line forms. When the steerable tip 142 is rotated in a yaw direction, it moves in an orthogonal direction to the illustrated dotted line forms. By rotating the steerable tip 142 in a combination of pitch and yaw, intermediate angles between pitch and yaw may be achieved. In this case, actuator 122 may steer the steerable tip 142 in pitch and actuator 123 may steer the steerable tip 142 in yaw. Alternatively, the steerable tip 142 may be rotated in roll about a central axis of the body 141 and one or both of pitch and yaw using corresponding actuators. The flexible body 141 may be passively bendable or actively bendable or a combination thereof. To actively bend the flexible body 141 additional actuators and control elements may be provided in addition to those already mentioned for steering the medical instrument 104.

When the medical instrument 104 is a steerable endoscope, it may have one or more lumens 145 through which a plurality of fiber optic cables 144 and an image capturing device 143 extend. The image capturing device 143 may be a stereoscopic or monoscopic camera for capturing images that are transmitted to and processed by an image processor 108 and displayed on a display screen 109 (shown in FIG. 4). Alternatively, the image capture device 143 may be a coherent fiber-optic bundle that couples to an imaging processing system on the proximal end of the instrument 104, such as a fiberscope. One of the fiber optic cables 144 may be coupled at its proximal end to a light source (not shown) for illumination purposes at the distal end of the medical instrument 104. Others of the fiber optic cables 144 may be configured with bend or shape sensors such as Fiber Bragg Gratings (or other strain sensors such as those employing Rayleigh scattering) so that light passing through the fiber optic cable is processed by the controller 102 to determine a current position and shape of the medical instrument 104 including the orientation of the steerable tip 142.

One example of such a steerable endoscope is described in WO 2009/097461 A1 entitled "Apparatus and methods for automatically controlling an endoscope," which is incorporated herein by reference. Details on the determination of the endoscope's position and bending using Fiber Bragg Gratings may be found, for examples, in U.S. 2007/0156019 A1 entitled "Robotic Surgery System Including Position Sensors Using Fiber Bragg Gratings", U.S. 2008/0212082 A1 entitled "Fiber Optic Position and/or Shape Sensing Based on Rayleigh Scatter", U.S. 2008/0218770 A1 entitled "Robotic Surgical Instrument and Methods using Bragg Fiber Sensors", and U.S. 2009/0324161 A1 entitled "Fiber Optic Shape Sensor", each of which is incorporated herein by reference.

Figure 3:
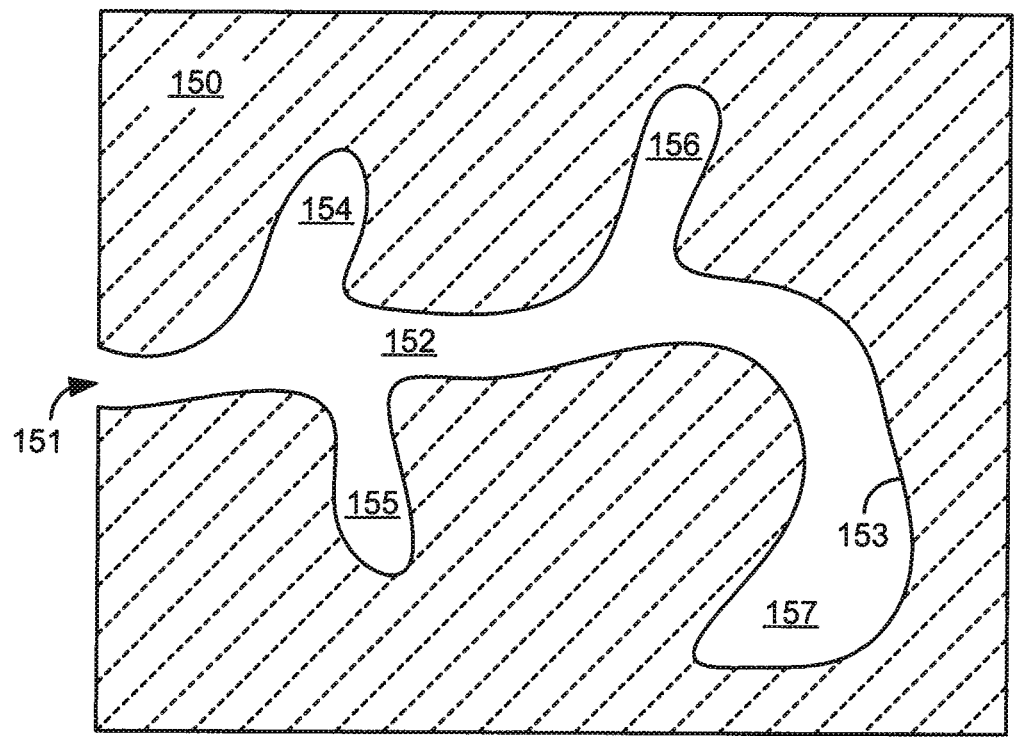

FIG. 3 illustrates a diagram of linked body passages 152 in a patient 150 through which the medical instrument 104 moves under control of the controller 102 in response to operator interaction with the input device 101. The linked body passages 152 has an entry point 151 through which the medical instrument 104 enters, branch passages 154, 155, 156, and 157 which provide paths for the medical instrument 104 to reach different target areas in the patient, and walls 153 of tissue. Although shown in FIG. 3 as a tree structure with multiple branch passages, the linked body passages 152 may instead comprise a single lumen or passage. In addition to natural body passages, artificial or surgeon created body passages may also be included among the linked body passages 152.

Figure 4:
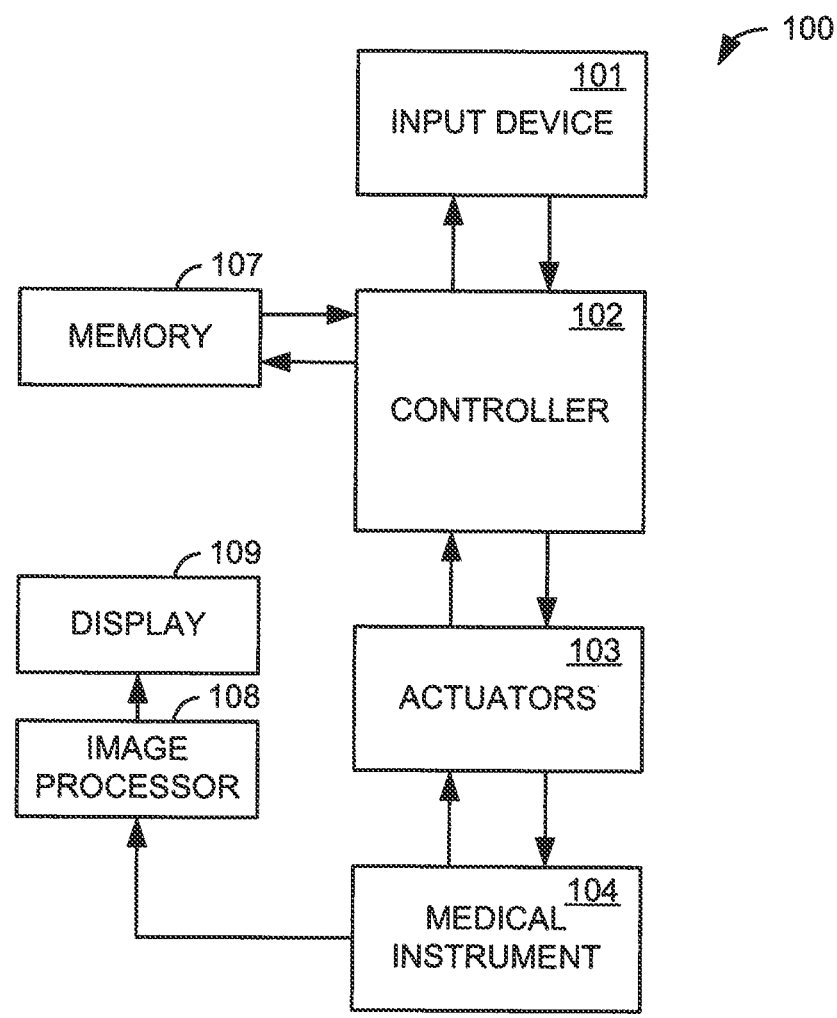
FIG. 4 illustrates a block diagram of a medical system utilizing aspects of the present invention.

FIG. 4 illustrates, as an example, a block diagram of the medical system 100. A controller 102 controls movement of a medical instrument 104 by commanding actuators 103 according to a current operating mode of the controller 102. The controller 102 may be implemented as one or more centralized or distributed processors executing program code stored in one or more memories, with each of the processors implemented in turn, by one or a combination, of hardware, firmware, and software. The current operating mode normally depends upon whether the operator is commanding movement of the medical instrument 104 in an insertion direction (i.e., into the patient) or a retraction direction (i.e., out of the patient). Default operating modes are provided so that the current operating mode is an automatic navigation mode when movement of the medical instrument 104 in the insertion direction is detected and the current operating mode is a zero-force mode when movement of the medical instrument 104 in the retraction direction is detected. The programmed default modes, however, may be manually overridden for safety, course alteration, or other purposes. An input device 101 is provided in the medical system 100 for manual steering of the medical instrument 104 when the automatic navigation mode is overridden. The input device 101 may also be used for commanding insertion and retraction of the medical instrument 104. Alternatively, such insertion and retraction may be performed by an operator manually moving the medical instrument 104 in the insertion and retraction directions. Also included in the medical system 100 are the actuators 103, the medical instrument 104, a memory 107, a display screen 109, and an image processor 108.

Figure 5:
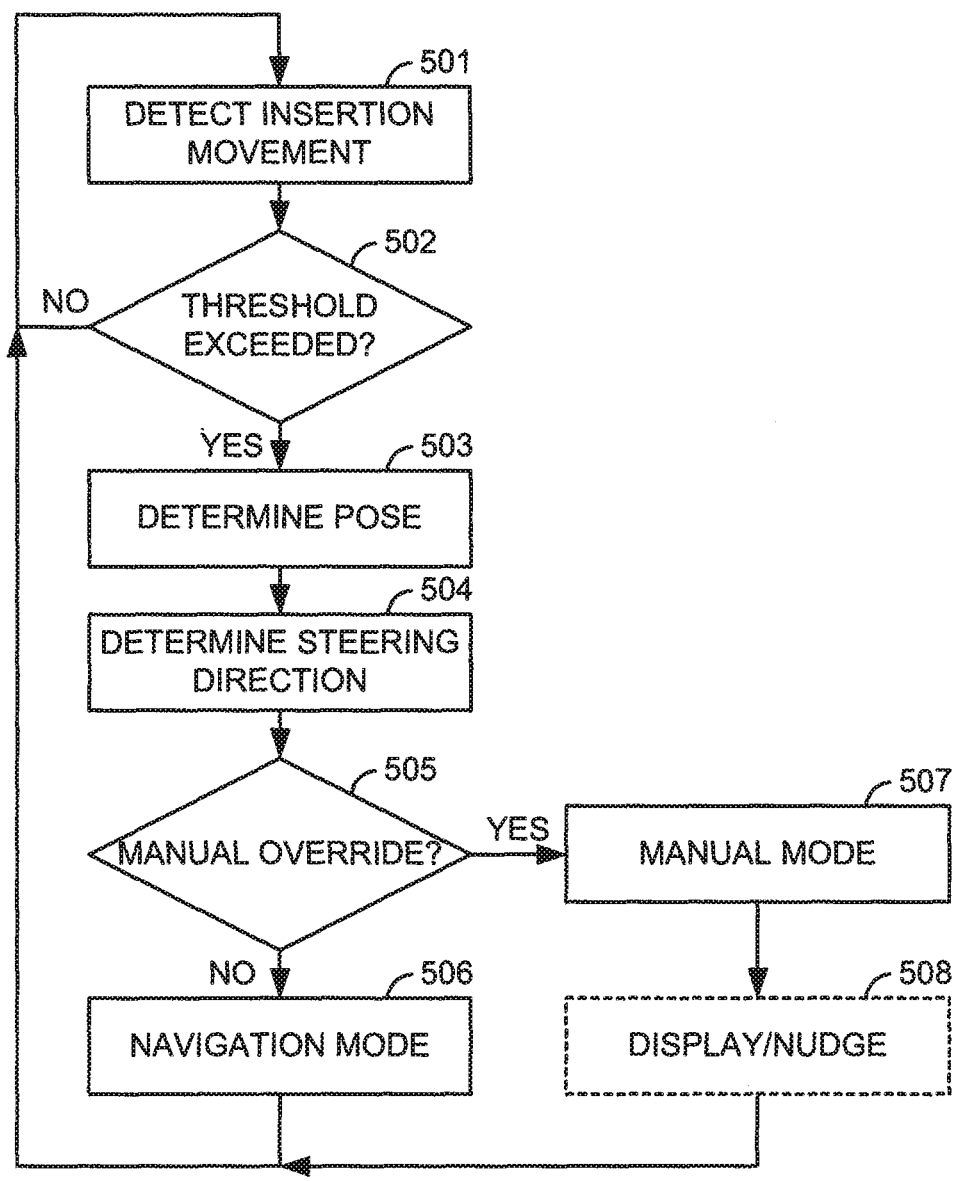
FIG. 5 illustrates a flow diagram of a method, utilizing aspects of the present invention, for controlling a medical instrument during its insertion towards a target area in a patient.

FIG. 5 illustrates, as an example, a flow diagram of a method performed by the controller 102 for controlling the steering of the medical instrument 104 during its insertion towards a target area in a patient. In block 501, the method detects movement of the medical instrument 104 in the insertion direction by either detecting movement of the input device 101 or movement of the medical instrument 104 using appropriate sensors. In block 502, the method determines whether the movement exceeds a threshold value to avoid false indications of operator intended insertion movement. Examples of such false indications include noise in the system or hand tremors when the operator is manually interacting with the input device 101 or manually inserting the medical instrument 104. The threshold values may be based upon either a change in position independent of time or a change in position over a specified period of time (i.e., a velocity).

If the determination in block 502 is NO, then the method loops back to block 501. On the other hand, if the determination in block 502 is YES, then the method proceeds to block 503 where it determines the current pose (i.e., position and orientation) of the distal tip 142 of the medical instrument 104. In block 504, the method next determines the steering direction according to a programmed navigation path using the current pose of the medical instrument 104. The navigation path may be determined pre-operatively or inter-operatively using images of the patient anatomy such as those generated using Computed Tomography (CT) scans, Magnetic Resonance Imaging (MRI) scans, and the like.

In normal operation, the method then proceeds to block 506 where it operates in an automatic navigation mode to command actuators 122 and 123 to steer the medical instrument 104 along the programmed navigation path according to the determined steering direction. After performing block 506, the method then proceeds by jumping back to block 501 to perform another process cycle.

The method is also provided with a manual override feature which is logically shown as block 505 (interposed between blocks 504 and 506) in which a determination is made whether the operator has activated a manual override. The operator may do this by activating a manual override switch located, for example, on the input device 101, or by simply moving the input device 101 so as to "overpower" the navigation mode and command the steering actuators 122 and 123 to steer the steerable tip 142 as desired. Overpower in this sense means that the operator has commanded through the input device 101 sufficient movement (e.g., exceeding a threshold amount) of the steerable tip 142 in a steering direction that is in contradiction to that of the navigation mode command. Although shown as a determination in block 505, the manual override may be implemented as a conventional "system interrupt" which causes the controller 102 implementing the method to jump to block 507 so as to allow manual mode operation in which the operator may take over control of steering the medical instrument 104. In particular, in manual mode operation, the controller 102 allows the operator full control of steering the steerable tip 142 of the medical instrument 104 by commanding the tip steering actuators 122 and 123 to steer the steerable tip 142 in response to operator interaction with the input device 101 that commands such steering action.

While operating in manual mode, block 508 may optionally be performed in which the method causes a graphical indication of the steering direction determined in block 504 to be shown in the display screen 109. Alternatively, or additionally, the method may cause a nudging force to be provided on the input device 101 so as to encourage the operator to steer the medical instrument 104 in the steering direction determined in block 504. When the operator desires to transfer control back to automatic navigation mode, the override may be released and the method jumps back to block 501. Subsequently, after performing a manual override, an updated navigation path may be determined using the current pose of the medical instrument as determined in block 503 and a new steering direction determined using the updated navigation path in block 504, since the medical instrument 104 may no longer be on the original navigation path following the manual override. In this way, each time the operator switches from manual to navigation mode, a new navigation path from the current instrument position to the target area may be determined in a manner similar to a car navigator which automatically re-computes the path to a destination when the driver drives off the navigation path. The navigation path (original and updated) may be stored in the memory 107 so that it is accessible to the controller 102.

Figure 6:
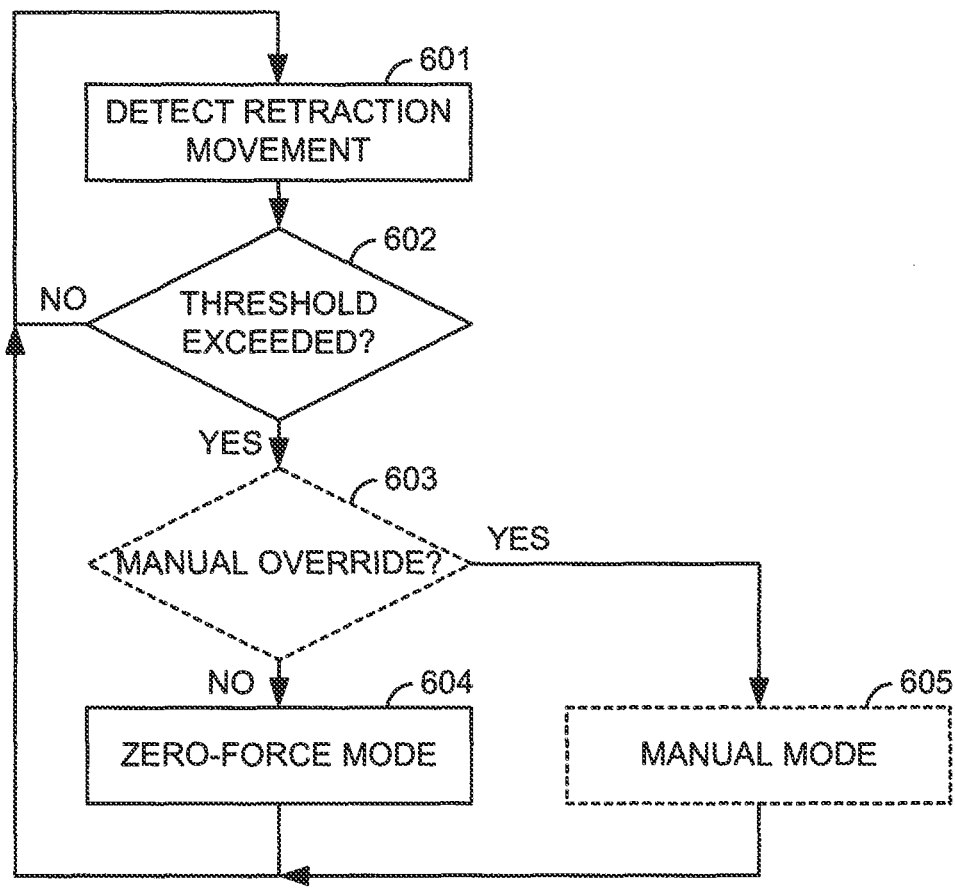
FIG. 6 illustrates a flow diagram of a method, utilizing aspects of the present invention, for controlling a medical instrument during its retraction away from a target area in a patient.

FIG. 6 illustrates, as an example, a flow diagram of a method performed by the controller 102 for controlling a medical instrument 104 during its retraction away from a target area in a patient. In block 601, the method detects movement of the medical instrument 104 in the retraction direction by either detecting movement of the input device 101 or movement of the medical instrument 104 using appropriate sensors. In block 602, the method determines whether the movement exceeds a threshold value to avoid false indications of operator intended retraction movement (such as previously described in reference to block 502 of FIG. 5). If the determination in block 602 is NO, then the method loops back to block 601.

In normal operation, the method then proceeds to block 604 where it operates in a zero-force mode to command actuators 122 and 123 to allow the medical instrument 104 to move in compliance with forces exerted against the medical instrument 104 (such as exerted by the passage walls as the medical instrument travels through a passage). For example, the controller 102 may actively control the steerable tip 142 so as to minimize contact forces with the walls 153 of the linked body passages 152 based upon detected interaction forces. As another example, the controller 102 may deactivate the steering actuators 122 and 123 so the steerable tip 142 is free to move in compliance with the walls 153 of the linked body passages 152. Thus, the passage walls which may be of sensitive tissue are subjected to only minimal harm during the retraction of the medical instrument 104. The method then proceeds by jumping back to block 601 to perform another process cycle.

The method is also optionally provided with a manual override feature which is logically shown as blocks 603 and 605. The manual override in this case would operate similarly to the manual override of blocks 505 and 507 as described in reference to FIG. 5. After completing the manual override, the method then jumps back to block 601 to re-enter normal mode retraction operation.

Regardless of which operating mode the controller 102 is operating in, it is noteworthy that the operator always has control over the direction and speed of the movement of the medical instrument 104. In particular, even when the controller 102 is automatically steering the steerable tip 142, the operator may stop all action by ceasing to command insertion of the medical instrument 104. The operator may also slow down such action by slowing down the commanded rate of the insertion.

Although the various aspects of the present invention have been described with respect to one or more embodiments, it will be understood that the invention is entitled to full protection within the full scope of the appended claims and is not to be limited by the described embodiments.

What is claimed is:

1. A medical system comprising:
   a steerable medical instrument defining a central axis therethrough, the steerable medical instrument comprising a steerable tip at a distal end thereof;
   at least one actuator; and
   control means for:
   commanding the at least one actuator to actively steer the medical instrument according to a programmed navigation path according to an insertion control mode as the medical instrument moves in an insertion direction along the central axis through an anatomic passageway;
   transitioning from the insertion control mode to a manual override control mode in response to movement of an operator input device that is in contradiction to the programmed navigation path; and
   while in the manual override control mode, displaying on a display screen a graphical indication of a steering direction corresponding to the programmed navigation path.

2. The medical system of claim 1, wherein the insertion control mode commands the at least one actuator to steer the medical instrument according to the programmed navigation path, wherein the programmed navigation path is determined pre-operatively.

3. The medical system of claim 2, wherein the programmed navigation path indicates a steering direction determined from a current insertion position of the medical instrument.

4. The medical system of claim 2, wherein the insertion control mode commands the at least one actuator to steer the medical instrument according to operator interaction with a control device if an operator overrides the programmed navigation path.

5. The medical system of claim 4, wherein the control means causes a nudging force to be exerted on the control device so as to indicate the steering direction corresponding to the programmed navigation path.

6. The medical system of claim 4, further comprising a display screen and an image capturing device, wherein the control means causes images captured by the image capturing device to be displayed on the display screen.

7. The medical system of claim 1, further comprising detection means for detecting movement of the medical instrument in the insertion direction by a change exceeding a threshold amount in the insertion direction.

8. The medical system of claim 1, further comprising detection means for detecting movement of the medical instrument in a retraction direction by a change exceeding a threshold amount in the retraction direction.

9. The medical system of claim 1, wherein the insertion control mode commands the at least one actuator to steer the medical instrument according to operator interaction with a control device.

10. The medical system of claim 9, wherein the control means causes a nudging force to be exerted on the control device so as to indicate the steering direction corresponding to the programmed navigation path.

11. The medical system of claim 1, wherein the steerable medical instrument is moved in the insertion and retraction directions by an operator manually pushing and pulling the steerable medical instrument into and out a passage.

12. A method for controlling steering of a medical instrument, the method comprising:
    receiving an indication of movement of the medical instrument along a central axis defined through the medical instrument; and
    commanding at least one actuator to actively steer a steerable tip of the medical instrument according to a programmed navigation path according to an insertion control mode as the medical instrument moves in an insertion direction along the central axis through an anatomic passageway
    transitioning from the insertion control mode to a manual override control mode in response to movement of an operator input device that is in contradiction to the programmed navigation path; and
    while in the manual override control mode, displaying on a display screen a graphical indication of a steering direction corresponding to the programmed navigation path.

13. A medical system comprising:
    an operator input device;
    a medical instrument;
    at least one insertion actuator;
    at least one steering actuator; and
    control means for commanding the at least one insertion actuator to move the medical instrument in an insertion direction in response to a movement of the operator input device commanding such insertion in a normal control mode and commanding the at least one steering actuator to steer the medical instrument according to a programmed navigation path in the normal control mode in response to the movement of the operator input device,
    for commanding the at least one steering actuator to cause the medical instrument to be steered according to another movement of the operator input device commanding such steering when the normal control mode is manually overridden by an operator of the operator input device, and
    for commanding the at least one steering actuator to steer the medical instrument according to an updated programmed navigation path based on a resulting pose of the medical instrument caused by the other movement of the operator input device, wherein the updated programmed navigation path is different that the programmed navigation path.

14. The medical system of claim 13, wherein the programmed navigation path indicates a steering direction determined from a current insertion position of the medical instrument and the updated programmed navigation path indicates a new steering direction.

15. The medical system of claim 13, wherein the control means causes a nudging force to be exerted on the operator input device so as to indicate a steering direction in conformance with the programmed navigation path.

16. The medical system of claim 13, further comprising a display screen, wherein the control means causes an indication of a steering direction in conformance with the programmed navigation path to be displayed on the display screen when the normal control mode is manually overridden.

17. The medical system of claim 13, wherein the control means detects movement of the medical instrument in the insertion direction by a change exceeding a threshold amount in the insertion direction.

18. The medical system of claim 13, wherein the medical instrument is moved in insertion and retraction directions by the operator manually pushing and pulling the medical instrument into and out of a passage.

19. A method for controlling steering of a medical instrument, the method comprising:

commanding at least one insertion actuator to move the medical instrument in an insertion direction in response to movement of an operator input device commanding such insertion and commanding at least one steering actuator to steer the medical instrument according to a programmed navigation path in response to the movement of the operator input device;

receiving a manual override indication based on another movement of the operator input device;

in response to the manual override indication, commanding the at least one steering actuator to steer the medical instrument according to the other movement of the operator input device such that the medical instrument has a resulting pose; and commanding the at least one steering actuator to steer the medical instrument according to an updated programmed navigation path based on the resulting pose of the medical instrument caused by the other movement of the operator input device, wherein the updated programmed navigation path is different from the programmed navigation path.

\* \* \* \* \*